United States Patent
Lansonneur et al.

(10) Patent No.: US 12,311,196 B2
(45) Date of Patent: May 27, 2025

(54) MONITOR UNIT OPTIMIZATION CONSTRAINT IN RADIATION TREATMENT PLANNING

(71) Applicant: Varian Medical Systems, Inc., Palo Alto, CA (US)

(72) Inventors: Pierre Lansonneur, Helsinki (FI); Tatu Heikki Leinonen, Helsinki (FI); Matti Sakari Ropo, Helsinki (FI); Jessica Perez, Geneva (CH); Michael Folkerts, Carrollton, TX (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 427 days.

(21) Appl. No.: 17/707,805

(22) Filed: Mar. 29, 2022

(65) Prior Publication Data

US 2023/0310888 A1  Oct. 5, 2023

(51) Int. Cl.
*A61N 5/10* (2006.01)
*G16H 20/40* (2018.01)

(52) U.S. Cl.
CPC ......... *A61N 5/1031* (2013.01); *A61N 5/1043* (2013.01); *G16H 20/40* (2018.01); *A61N 2005/1087* (2013.01)

(58) Field of Classification Search
CPC ............... A61N 5/1031; A61N 5/1043; A61N 2005/1087; G16H 20/40
See application file for complete search history.

(56) References Cited

U.S. PATENT DOCUMENTS

| | | |
|---|---|---|
| 2010/0020931 A1 | 1/2010 | Otto et al. |
| 2018/0020535 A1* | 1/2018 | Cooley ............... A61N 5/1037 |
| 2019/0255355 A1* | 8/2019 | Nordström ........... A61N 5/1071 |
| 2020/0105395 A1 | 4/2020 | Huth et al. |
| 2020/0121949 A1* | 4/2020 | Kamiguchi .......... A61N 5/1049 |
| 2020/0129781 A1* | 4/2020 | Engwall ............. A61N 5/1043 |
| 2020/0129782 A1* | 4/2020 | Stål ..................... A61N 5/1067 |
| 2020/0164225 A1 | 5/2020 | Zhang et al. |
| 2021/0052917 A1 | 2/2021 | Vanderstraeten et al. |

FOREIGN PATENT DOCUMENTS

EP       3881895 A1    9/2021

* cited by examiner

*Primary Examiner* — Sean M Luck
(74) *Attorney, Agent, or Firm* — Harness, Dickey & Pierce, P.L.C.

(57) ABSTRACT

For planning radiation treatment, candidate radiation treatment plans are evaluated and optimized using an objective function that includes a combination of a first objective function and a second objective function. The first objective function is configured for determining a value of a dose metric. The second objective function is configured for determining a value of a term that is added to the value of the dose metric to account for spots or beam lets that have a weight that is greater than zero and less than a minimum threshold value. The value of the term is added to the value of the dose metric. In effect, spots or beam lets with a weight that is not zero and that is also less than a minimum threshold value are penalized during treatment planning.

20 Claims, 6 Drawing Sheets

MONITOR UNIT OPTIMIZATION CONSTRAINT IN RADIATION TREATMENT PLANNING

BACKGROUND

The use of radiation therapy to treat cancer is well known. Typically, radiation therapy involves directing a beam of high energy proton, photon, ion, or electron radiation into a target volume in a treatment target of unhealthy tissue (e.g., a tumor or lesion).

Radiation therapy using proton beams (proton therapy) has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The treatment plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

One radiation therapy technique is known as spot scanning, also referred to as pencil beam scanning. In spot scanning, a beam is directed to spots in a treatment target as prescribed by the treatment plan. The prescribed spot locations are typically arranged in a fixed (raster) pattern for each energy layer of the beam, and the beam is delivered on a fixed scanning path within an energy layer. By superposition of several beams of different energies at neighboring spots, the Bragg peaks of the beams overlap to deliver the prescribed dose across the treatment target up to the edges of the target, with a sharp drop in dose beyond the edges.

During development of a treatment plan, a spot pattern is specified for the treatment target, and the treatment plan is then optimized by, among other things, adjusting the weights of the spots in the pattern to meet dosimetric constraints. In proton therapy, the weight of each spot may be expressed as a value of a monitor unit (e.g., number of protons).

For a number of reasons, the treatment planner may want the adjusted or optimized weights to be above a minimum value. Those reasons include, for example, limitations of the treatment system (e.g., the system cannot deliver dose rates or MUs that are too small), delivery of higher dose rates per spot (e.g., FLASH dose rates of 20-40 grays (Gy) delivered in less than one second, and as much as 120 or more Gy per second), reduction of the number of spots that are to be irradiated, and/or reduction of delivery (treatment) times per spot.

However, developing a high-quality treatment plan and enforcing a minimum value of spot weight are competing interests. For example, if the minimum value is set too high, then the number of spots that are irradiated may be lower than an optimum value, thereby negatively affecting the projected dose-volume histogram (DVH). On the other hand, if the minimum value is set too low, then the number of spots that are irradiated may be higher than an optimum value, thereby lengthening the treatment time (dose delivery time) to the detriment of the patient.

SUMMARY

Embodiments according to the present invention provide solutions to the problems described above by introducing an additional constraint into the treatment planning process. In general, when generating, evaluating or optimizing radiation treatment plans, embodiments disclosed herein penalize spots or beam lets with a monitor unit (MU; e.g., a spot weight or beam let weight) that is below a certain value. As examples, an MU for a spot weight may be based on a number of particles for the spot, and an MU for a beam let weight may be based on an energy or intensity for the beam let.

More specifically, when generating or evaluating a radiation treatment plan in embodiments according to the present disclosure, weights assigned to the spots inside the treatment target, or weights assigned to beam lets to be directed into the treatment target during treatment, are determined or accessed from computer system memory. A first objective function configured for determining a value of a dose metric is accessed from computer system memory. A second objective function configured for determining a value of a term as a function of the MU value (e.g., a measure of spot weight or beam let weight) is also accessed from computer system memory. A proposed or candidate radiation treatment plan is evaluated using an objective function that includes a combination of the results of the first objective function and the second objective function. For example, a sum of a result of the first objective function and a result of the second objective function is used in the optimization phase of the treatment planning process. In that example, the value of the term determined with the second objective function is added to the value of the dose metric determined with the first objective function, and that sum is used in the optimization process. The optimization process produces a final radiation treatment plan that includes final spot weights or beam let weights.

In an embodiment, the value of the second objective function is: equal to zero when the value of the MU (e.g., spot weight or beamlet weight) for a spot or a beam let is equal to zero; equal to zero when the value of the MU for a spot or a beamlet is equal to or greater than the minimum threshold value; and greater than zero when the value of the MU for a spot or a beamlet is between zero and the minimum threshold value. The value of the term determined with the second objective function is the summation of these values across all of the spots or beamlets. Thus, the value of the term is greater than zero when one or more of the spots or beam lets has an MU value between zero and the minimum threshold value. In effect, a non-zero value of the term penalizes spots or beamlets with weights between zero and the minimum threshold value during the optimization process, because a goal of that process is to minimize the combination (e.g., sum) of the first and second objective functions.

As a result of incorporating that penalty into the optimization process, the optimized radiation treatment plan will include only a small number of spots or beamlets with a weight that is between zero and the minimum threshold value, or will include no such spots or beamlets at all. If the optimized radiation treatment plan includes spots or beam lets with a weight in the range between zero and the minimum threshold value, those spots or beam lets can be optionally post-processed to remove them from that range (e.g., their weights/MU values can be set to either zero or the minimum threshold value).

Embodiments according to the present disclosure provide methods that can be used for generating radiation treatment plans for radiation therapy (RT) including FLASH RT. For FLASH RT, doses above 40 grays (Gy) delivered in less than one second may be used.

Thus, spot weights or beamlet weights can be automatically adjusted by a treatment planning system to satisfy limitations of the treatment system, deliver higher dose rates per spot (e.g., FLASH dose rates), reduce the number of spots that are to be irradiated during treatment, reduce the number of beam lets needed for treatment, and/or reduce delivery (treatment) times per spot or beamlet. Consequently, embodiments according to the present disclosure improve the field of radiation treatment planning specifically and the field of radiation therapy in general.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments according to the present disclosure and, together with the detailed description, serve to explain the principles of the disclosure. The drawings are not necessarily drawn to scale.

DETAILED DESCRIPTION

Figure 1:
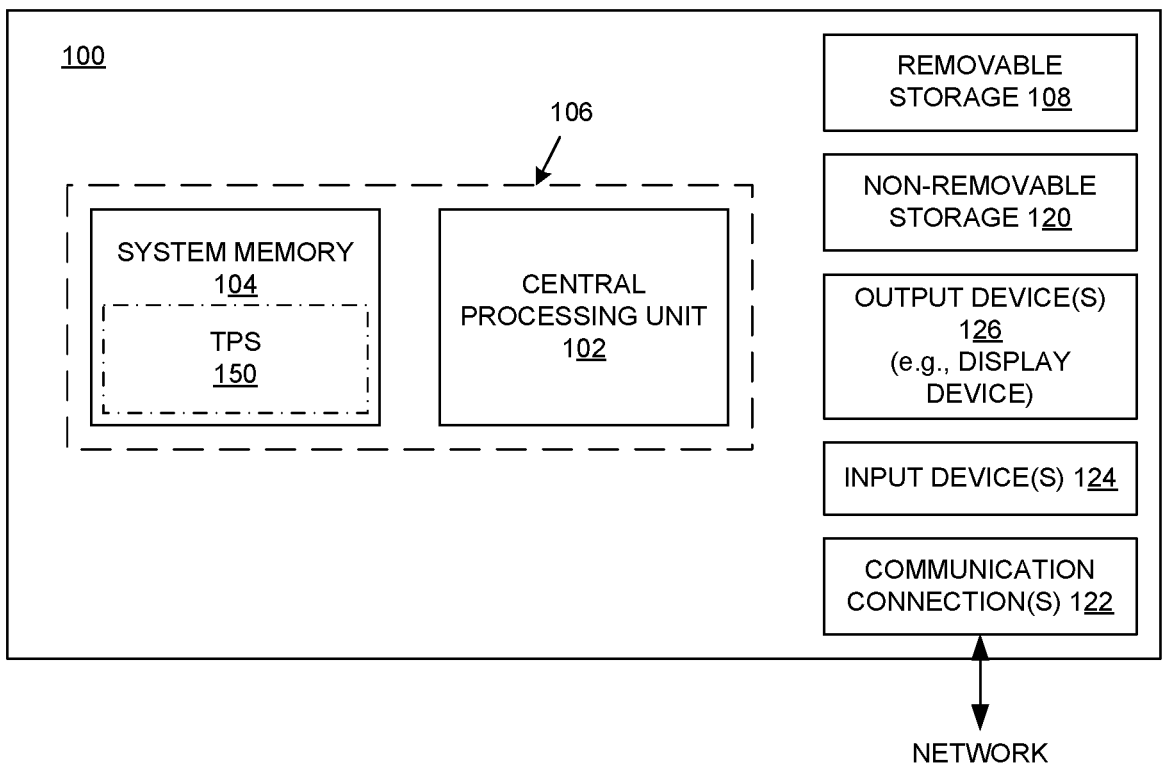
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "storing," "assigning," "adjusting," "combining," "summing," "adding," "optimizing," "minimizing," producing," "generating," "identifying," "setting," "increasing," "evaluating," "calculating," or the like, refer to actions and processes (e.g., the flowcharts of FIGS. 8 and 9) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow may include terms such as "weight," "metric," "intensity," "monitor unit," etc. Unless otherwise noted, a value is associated with each such term. For example, a weight (e.g., a weight of a spot or beamlet) has a value, and a metric has a value. For simplicity, the term "weight" or "metric" or "intensity" or "monitor unit" may refer to a value of the weight or metric or intensity or MU itself, unless otherwise noted or apparent from the discussion.

Portions of the detailed description that follows are presented and discussed in terms of methods or processes. Although operations and sequencing thereof are disclosed herein, such operations and sequencing are examples only. Embodiments are well-suited to performing various other operations or variations of the operations described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as a keyboard, mouse, pen, voice input device, touch input device, etc. Output device(s) 126 such as a display device, speakers, printer, etc., are also included. A display device may be, for example, a cathode ray tube display, a light-emitting diode display, or a liquid crystal display.

Introduction

In the example of FIG. 1, the memory 104 includes computer-readable instructions, data structures, program modules, and the like associated with a treatment planning system (TPS) 150, which may also be referred to as an optimizer. However, the TPS 150 may instead reside in any one of the computer storage media used by the computer system 100, or may be distributed over some combination of the computer storage media, or may be distributed over some combination of networked computers. The TPS 150 is used to generate and evaluate candidate (proposed) treatment plans and produce a final (optimized) treatment plan.

More specifically, a proposed radiation treatment plan is defined (e.g., using the TPS 150 of FIG. 1), stored in a computer system memory, and accessed from that memory. Treatment modalities include intensity modulated radiation therapy (IMRT) and intensity modulated particle therapy (IMPT).

In IMRT embodiments, a proton, ion, or photon beam includes a number of beam segments or beam lets. The beam is shaped using multi-leaf collimators (MLCs) either before or while the beam is directed into the treatment target. In one or more such embodiments, a maximum energy (e.g., 80 MeV) for the beam is specified, and an energy for each of the beamlets is determined as a percentage (100 percent or less) or equivalent fraction of the maximum beam energy. Thus, each of the beamlets can be weighted based on its energy level. By weighting based on the energy per beam let, each beam let is in effect also weighted based on its intensity.

In IMPT (e.g., spot scanning) embodiments, a proton or ion beam is directed to spots in a treatment target as prescribed by the treatment plan. The prescribed spot locations are typically arranged in a fixed (raster) pattern for each energy layer of the beam, and the beam is delivered on a fixed scanning path within an energy layer. Each spot can be weighted based on, for example, the number of protons it receives when irradiated by the beam.

The proposed radiation treatment plan includes values of parameters that can affect dose and/or dose rate, as well as other parameters. Depending on the treatment modality, the parameters may include, but are not limited to: beam shape (collimation); number and arrangement of spots for spot (pencil beam) scanning, and spot weights; beam let weights; beam let intensities or energies; beam/beam let directions; prescribed dose and prescribed dose rate; a number of irradiations of a target volume; a duration of each of the irradiations (irradiation times); and a dose deposited in each of the irradiations. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day).

The large number of parameters and their ranges of values can lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

To deliver the prescribed dose/dose rate of radiation, the radiation treatment plan may be converted (e.g., by the TPS 150) into machine parameters. Machine parameters can include, for example, beam currents of a proton, ion, or photon beam, the number of protons, ions, or photons per time segment to be emitted by the accelerator, magnet currents, settings to achieve the prescribed energy of protons, ions, or photons at the target volume, and the measurement range of a dose monitor system. This conversion thus takes into account the limitations of the treatment machine's equipment that produces the beam and that delivers and monitors the radiation treatment.

During treatment, in an example embodiment, a beam enters a nozzle of a radiotherapy machine, which may include one or more components that affect (e.g., decrease, modulate) the energy of the beam, to control the dose/dose rate delivered by the beam and/or to control the dose versus depth curve of the beam, depending on the type of beam. For example, for a proton beam or an ion beam that has a Bragg peak, the nozzle can control the location of the Bragg peak in the treatment target laterally to the beam axis. In other embodiments, energy modulation is performed outside of the nozzle (e.g., upstream of the nozzle).

In embodiments, the nozzle is mounted on a moveable gantry so that the beam can be delivered from different directions (angles) relative to a patient (treatment target) on the patient support device, and the position of the patient support device relative to the beam may also be changed.

Figure 2A:
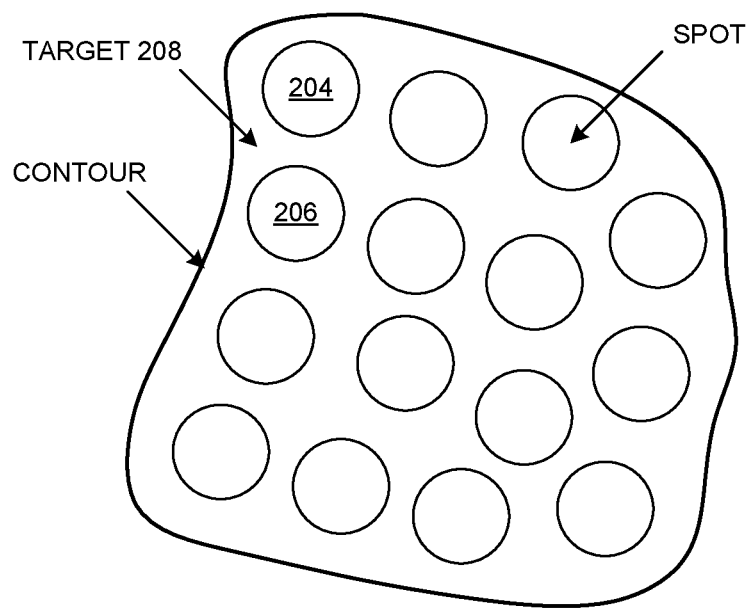
FIGS. 2A and 2B illustrate examples of a beam's eye view of a treatment target in embodiments according to the present disclosure.

FIG. 2A illustrates an example of a beam's eye view of a treatment target 208 in some (e.g., IMPT) embodiments according to the present disclosure. The treatment target 208 can coincide with the shape of the volume being treated (e.g., the contour of the treatment target can coincide with the contour of a tumor), the treatment target may be larger than the volume being treated, or the treatment target may correspond to a portion (e.g., a sub-volume) of the volume being treated.

In these embodiments, an arrangement of spots (e.g., the spots 204 and 206) is mapped onto the treatment target 208. Each spot corresponds to a particular location in the treatment target 208. The spots in the treatment target 208 may be irradiated with a raster scan (two-dimensional emission) of a spot scanning beam (pencil beam). Generally speaking, a first pencil beam is aimed at the first spot 204 in the treatment target 208, a dose rate is delivered to that spot, then a second pencil beam is aimed at the second spot 206 in the treatment target, a dose rate is delivered to the second spot, and so on. Spots with a weight or MU value of zero are not irradiated.

Each spot scanning beam can deliver a relatively high dose rate (a relatively high dose in a relatively short period of time) to each spot. For example, if necessary, the spot scanning beam can deliver above 40 grays (Gy) in less than one second to each spot.

Figure 2B:
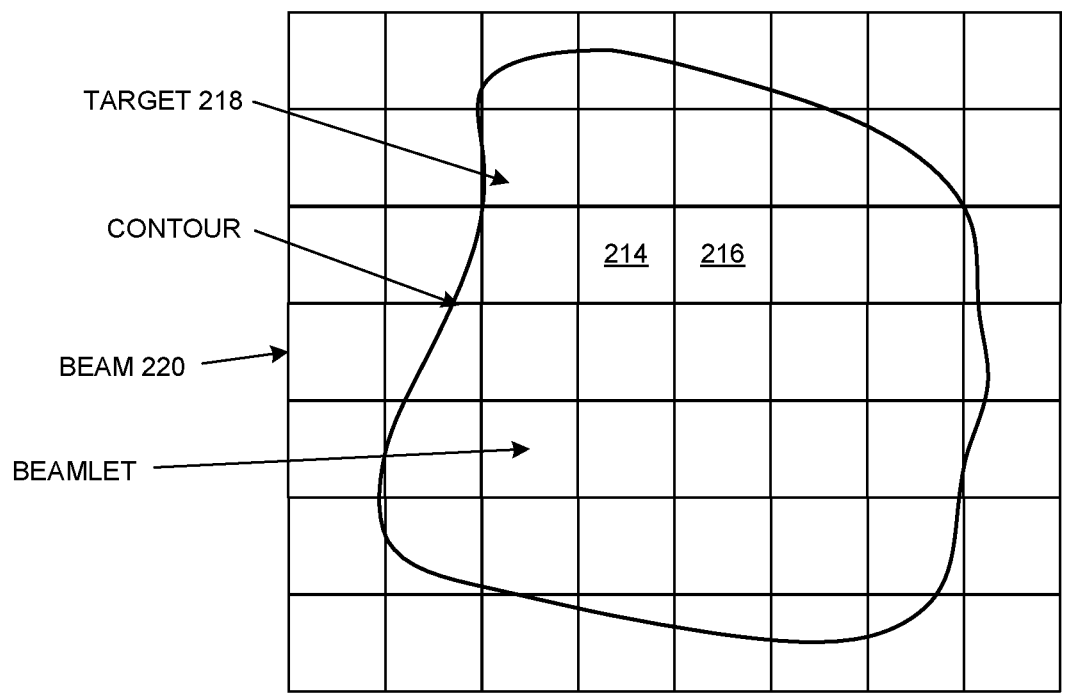

FIG. 2B illustrates an example of a beam's eye view of a treatment target 208 in other (e.g., IMRT) embodiments according to the present disclosure. In these embodiments, the beam 220 that is used to irradiate the treatment target 208 includes an array of beam lets (e.g., the beam lets 214 and 216) that is mapped onto the treatment target 208. Each beam let corresponds to a particular location in the treatment target 208. A maximum energy for the beam 220 is specified, and an energy for each of the beam lets 214, 216, etc., is determined as a percentage or fraction of the maximum beam energy.

Each beamlet can deliver a relatively high dose rate (a relatively high dose in a relatively short period of time). For example, if necessary, each beam let can deliver above 40 grays (Gy) in less than one second. Beam lets with a weight or MU value of zero are not used during treatment.

Automated Radiation Treatment Planning Processes

Figure 3:
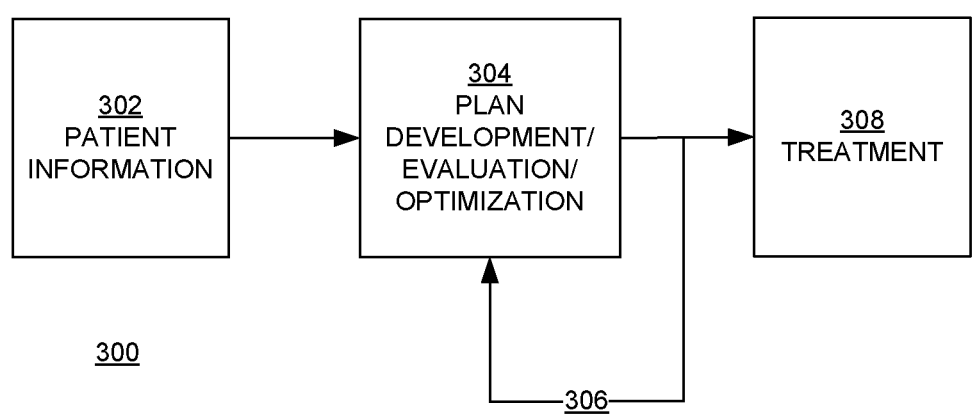
FIGS. 3 and 4 are block diagrams illustrating examples of an automated radiation therapy treatment planning process in embodiments according to the present disclosure.

FIG. 3 is a block diagram illustrating an example of an automated radiation therapy treatment planning process 300 in embodiments according to the present disclosure. The process 300, in whole or in part, may be implemented as a software program, hardware logic, or a combination thereof on/using the computer system 100 (FIG. 1).

In block 302 of FIG. 3, three-dimensional (3D) images of a patient are obtained, and organs and other structures in the patient (the patient geometry) can be segmented and contoured. In blocks 304 and 306, that information, and other information such as that mentioned above, are used to develop and evaluate a treatment plan, as described further below in conjunction with FIG. 4.

In block 308, if the treatment plan is satisfactory (e.g., it satisfies clinical goals), then the plan can be used for treatment of the patient. If not, then aspects of the treatment plan and/or of the clinical goals may be modified iteratively until a satisfactory plan is generated. The clinical goals may be expressed in terms of, for example, a set of quality metrics, such as target homogeneity, conformity to the treatment target, critical organ sparing, and the like, with respective target values for the quality metrics.

Figure 4:
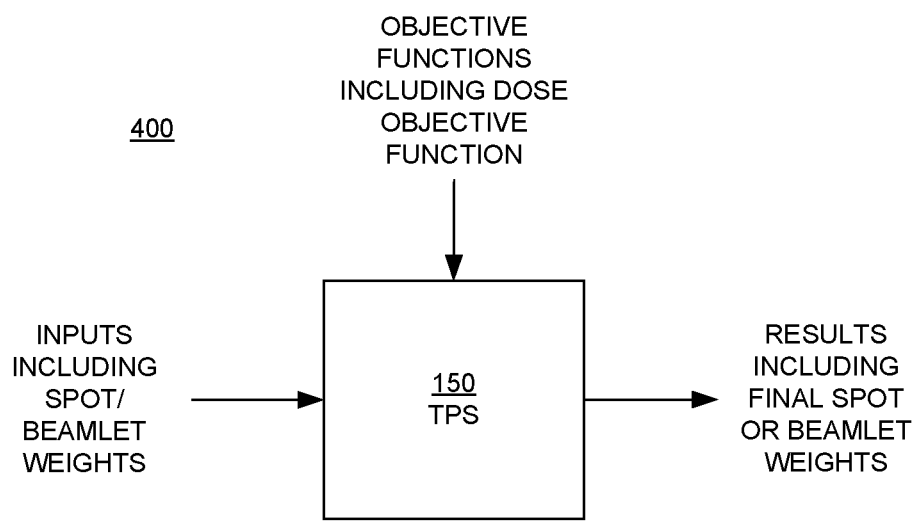

FIG. 4 is a block diagram illustrating an example of an automated radiation therapy treatment planning process 400 in embodiments according to the present disclosure. The process 400, in whole or in part, may be implemented as a software program, hardware logic, or a combination thereof on/using the computer system 100 (FIG. 1). The process 400 corresponds generally to blocks 304 and 306 of FIG. 3.

In the example of FIG. 4, the TPS 150 accesses or receives (e.g., from the memory 104 of FIG. 1) information that includes parameters such as those mentioned above. The TPS 150 can also access or receive information specific to the patient to be treated (e.g., patient geometry), including information that describes a treatment target (region of interest, ROI), which can include a planned target volume (PTV), gross tumor volume (GTV), clinical target volume (CTV), and organs-at-risk (OARs).

The TPS 150 also accesses or receives objective functions defined for the treatment of the patient. Objective functions are mathematical formulations of variables (parameters such as those mentioned above) that can have an effect on achieving specified clinical goals. More specifically, the objective functions are used to evaluate proposed radiation treatment plans, to determine whether or not the clinical goals that are specified for treatment of a patient are satisfied.

An example of a dose objective function $f(d)$ is: $f(d)=\Sigma (w_i)(d_i-d_p)^2$, where $w_i$ is a weight per voxel in a treatment target, $d_i$ is the dose per voxel projected to be received according to a proposed treatment plan, $d_p$ is the prescribed dose per voxel, and the summation $\Sigma$ is over all voxels i in the treatment target. A voxel can be a spot in the treatment target irradiated by a spot scanning beam, or can correspond to a location in the treatment target into which a beamlet is directed. In this example, the goal is to minimize the value of the dose objective function (in this example, the dose across the treatment target becomes more uniform as the value of the function is decreased). In practice, there may be several objective functions (in addition to the dose objective function) that are to be minimized in order to achieve an optimal final treatment plan. The objective functions may conflict with each other; that is, minimizing one objective function may penalize another objective function, and so minimizing all of the objective functions may not be achievable. Thus, in embodiments, the objective functions are weighted and summed to provide a total of all of the objective functions, and that total is then minimized.

Of particular interest to this disclosure are spot weights and beam let weights, and an objective function that is associated with or affected by the spot weights or beamlet weights. That objective function may be referred to herein generally as the dosimetric objective function.

With reference again to FIG. 4, in some (e.g., IMPT) embodiments, the information accessed or received by the TPS 150 includes, but is not limited to, the number and positions (pattern or arrangement) of spots, a value (e.g., an initial value) of a weight for each spot in the treatment target, and a dosimetric objective function that accounts for the dose objective for the PTV and OARs. The weight of each spot may be expressed as a value of a monitor unit (MU) corresponding to, for example, the number of particles (e.g., protons or ions) per spot. As noted above (see the discussion of FIG. 2A), each spot corresponds to a location in the treatment target. As such, each spot weight can be referred to as a "locational" weight or location-based weight: a spot corresponds to a location, a weight corresponds to the spot, and thus the spot weight corresponds to the location. In essence, in these embodiments, a spot weight is assigned to or associated with a respective location inside the treatment target.

In other (e.g., IMRT) embodiments, the information accessed or received by the TPS 150 includes, but is not limited to, the number of beamlets, a value (e.g., an initial value) of a weight for each beamlet (where the weight corresponds to a fraction or percentage of the beam energy), and a dosimetric objective function that accounts for the dose objective for the PTV and OARs. The weight of each beam let may be expressed as a value of an MU corresponding to, for example, the beam let's intensity or energy as a fraction or percentage of beam intensity or energy. As noted above (see the discussion of FIG. 2B), each beamlet corresponds to a location in the treatment target. Similar to that of a spot weight, each beamlet weight can be referred to as a locational weight or location-based weight: a beamlet corresponds to a location, a weight corresponds to the beam let, and thus the beam let weight corresponds to the location. In essence, in these embodiments, a beamlet weight is assigned to or associated with a respective location inside the treatment target.

When generating and optimizing the treatment plan, the TPS 150 can adjust the weights of the spots or beamlets with respect to, for example, the dosimetric objective function. Along with the goals already mentioned herein, another goal is to determine and output a set of final weights so that, during treatment, the treatment target will receive a homogenous dose (a uniform dose across the treatment target) and the delivered dose will conform more closely to the edges of the treatment target.

Monitor Unit Optimization Constraint in Radiation Treatment Planning

In overview, in embodiments according to the present disclosure, an additional constraint is introduced into the treatment planning process. In general, embodiments disclosed herein penalize spots or beam lets with a weight (e.g., an MU value) that is below a certain value when generating or evaluating radiation treatment plans.

More specifically, a dose-based objective function f_D that accounts for dose objectives (e.g., OAR and PTV dose objectives) is formulated. Another objective function, referred to herein as the minimum MU objective function f_MU, is also formulated. The dose-based objective function f_D may be referred to herein as the first objective function, and the minimum MU objective function f_MU may be referred to herein as the second objective function.

As will be understood from the discussion to follow, f_MU introduces a constraint on the optimization process that penalizes spots or beam lets with MUs below a threshold (minimum) value. The combination of the values of the first and second objective functions, referred to herein as the total objective function f_total, is then used in the optimization process. Specifically, the total objective function is the sum of the values of the dose-based (first) objective function and the minimum MU (second) objective function, summed across all spots or beam lets: f_total=f_D+f_MU.

An example of a dose-based objective function f_D is given above. An example of the minimum MU objective function is given by:

$$f\_MU = \frac{1}{N}\sum_{j=1}^{N} f_{MU}(MU_j);$$

where N is the number of spots or beamlets. An example of $f_{MU}(MU_j)$ is presented below (see FIG. 5).

In general, the value of $f_{MU}(MU_j)$ for a spot or beam let is: zero for a spot j or beamlet j that has an MU (spot or beam let weight) of zero; zero for a spot j or beam let j with an MU (spot or beam let weight) greater than or equal to a minimum threshold value; and non-zero for a spot j or beamlet j with an MU (spot or beam let weight) between zero and the minimum threshold value. Thus, the value of f_total will be increased by spots with a spot weight, or beam lets with a beamlet weight, between zero and the minimum threshold value. Because a goal of the optimization process is to minimize the value of f_total (to the extent permitted by the interaction with other objective functions), spots with a spot weight, or beam lets with a beam let weight, between zero and the minimum threshold value are penalized during the optimization process.

Figure 5:
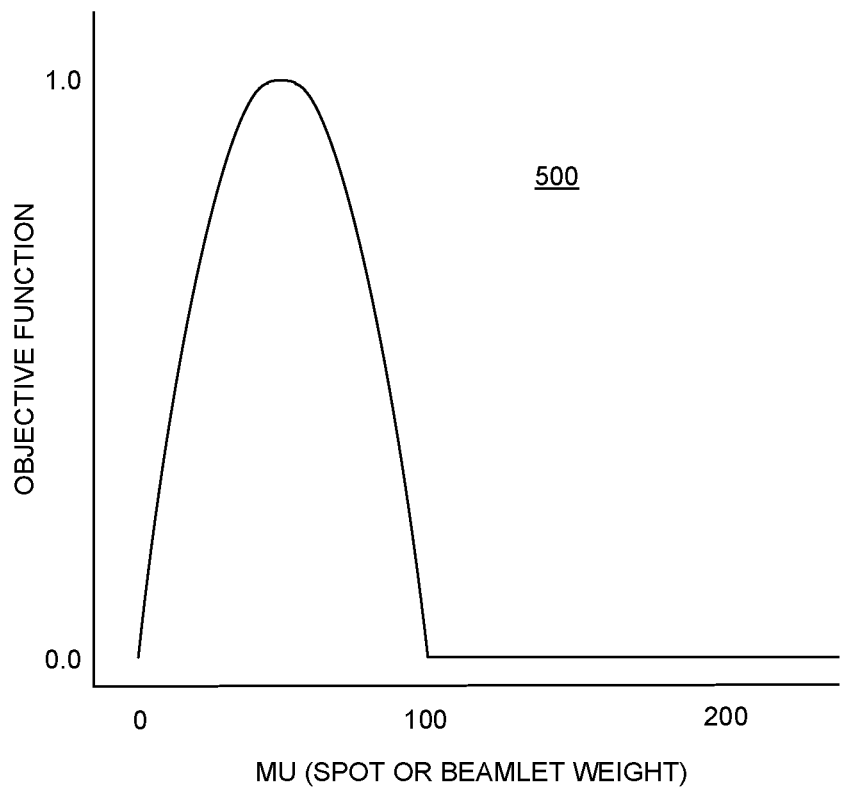
FIG. 5 is a graphical representation of an example of a minimum monitor unit (MU) objective function in embodiments according to the present disclosure.

FIG. 5 is a graphical representation of an example of a minimum MU objective function 500 in embodiments according to the present disclosure. In the example of FIG. 5, the minimum MU objective function 500 is defined by the formula:

$$f_{MU}(MU_j) = (4x_j/MU_{min})(1 - (x_j/MU_{min}));$$

where x is the spot or beamlet weight (in value of MUs) of a spot j or a beamlet j, and $MU_{min}$ is the minimum value of MU (the minimum threshold value, MU_min). However, the formulation of $f_{MU}(MU_j)$ is not limited to this example.

The minimum MU objective function is configured (formulated) to determine a value of f_MU that is added to the value of f_D to account for spots or beam lets that have a weight (MU) that is greater than zero and less than the minimum threshold value. The value of f_MU may be referred to herein as the value of a term (e.g., the term $$\frac{1}{N}\Sigma_{j=1}^{N} f_{MU}(MU_j)),$$

and the value of f_D may be referred to herein as the value of a dose metric. Here, the weight of a spot or beam let can be its initial weight, or it can be an intermediate (non-final) value that is determined iteratively as part of the optimization process.

In embodiments, the value of $f_{MU}(MU_j)$ for a spot j or a beam let j with a weight that is greater than zero and less than the minimum threshold value is a function of the weight of that spot or beamlet. In embodiments, the value of $f_{MU}(MU_j)$ is: equal to zero when the spot's or the beamlet's weight is equal to zero (f_MU(x=0)=0), equal to zero when that weight is equal to or greater than the minimum threshold value (f_MU(x≥MU_min)=0), and greater than zero when that weight is between zero and the minimum threshold value.

In the example of FIG. 5, the minimum MU objective function 500 is symmetrical (e.g., parabolic). However, embodiments according are not so limited. The minimum MU objective function can be asymmetrical or can have a constant value between zero and the threshold value, as examples. The maximum value of the minimum MU objective function can be different from (e.g., less than or greater than) the value of 1.0 in the example, and that maximum value can remain the same or can be changed (increased or decreased) during the optimization process. Also, the minimum threshold value can be a value other than 100. In embodiments, the minimum threshold value is a value selected by the treatment planner, and can remain the same or can be changed during the optimization process.

Furthermore, the formula defining the minimum MU objective function can be changed during the optimization process or can be kept the same throughout that process. Also, if there are multiple proposed (candidate) treatment plans to be evaluated for a particular patient, the minimum MU objective function and/or the minimum threshold value can be the same or different for each treatment plan being optimized.

In embodiments, a priority value is associated with each structure or volume in the treatment target, and a priority value is also associated with the minimum MU objective function. For example, a priority value may be associated with the PTV, and a priority value may be associated with the GTV. In such an embodiment, a priority value is similarly associated with the minimum MU objective function, to establish the relative priority of that objective function to the structures or volumes in the treatment target. The priority values are selected by the treatment planner, and can remain the same or can be changed during the optimization process.

Figure 6:
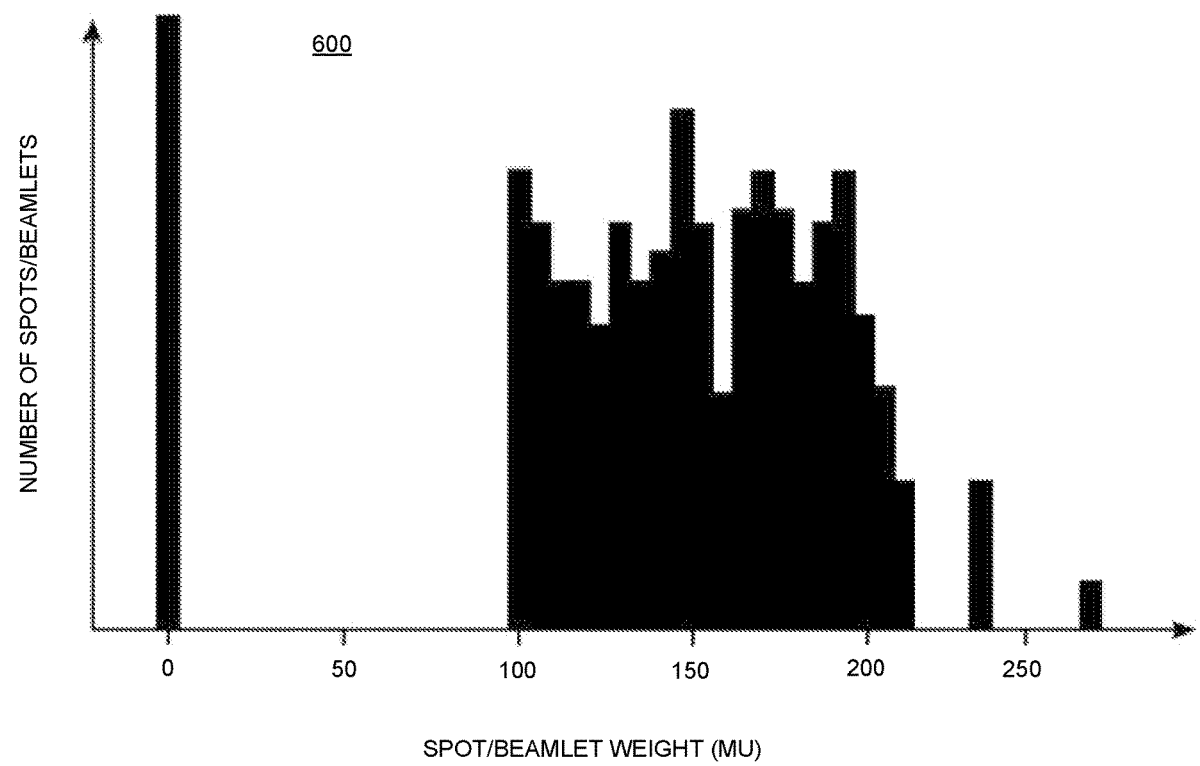
FIG. 6 is a histogram showing an example of the distribution of weights (MUs) that is a result of the use of a minimum MU objective function in radiation treatment planning in embodiments according to the present disclosure.

FIG. 6 is a histogram 600 showing an example of the distribution of MUs (e.g., spot weights or beamlet weights) that is a result of the use of the minimum MU objective function 500 of FIG. 5 in the optimization process in radiation treatment planning in embodiments according to the present disclosure. As can be seen in the figure, there are no MUs with a value between zero and 100 (the minimum threshold value in this example) in the optimized treatment plan.

Thus, as illustrated by the example of FIG. 6, spot weights or beamlet weights can be automatically adjusted by the TPS 150 to satisfy limitations of the treatment system, deliver higher dose rates per spot (e.g., FLASH doses above 40 Gy delivered in less than one second), reduce of the number of spots that are to be irradiated during treatment, reduce the number of beamlets used for treatment, and/or reduce delivery (treatment) times. Consequently, embodiments according to the present disclosure improve the field of radiation treatment planning specifically and the field of radiation therapy in general.

The lack of spots or beamlets with weights (MUs) in the range between zero and the minimum threshold value as in the example of FIG. 6 may not always be the result. In other words, after optimization, there may be spots or beam lets with weights within that range, in which case spot or beamlet weights between zero and the minimum threshold value can be optionally removed in post-processing as described below.

Figure 7:
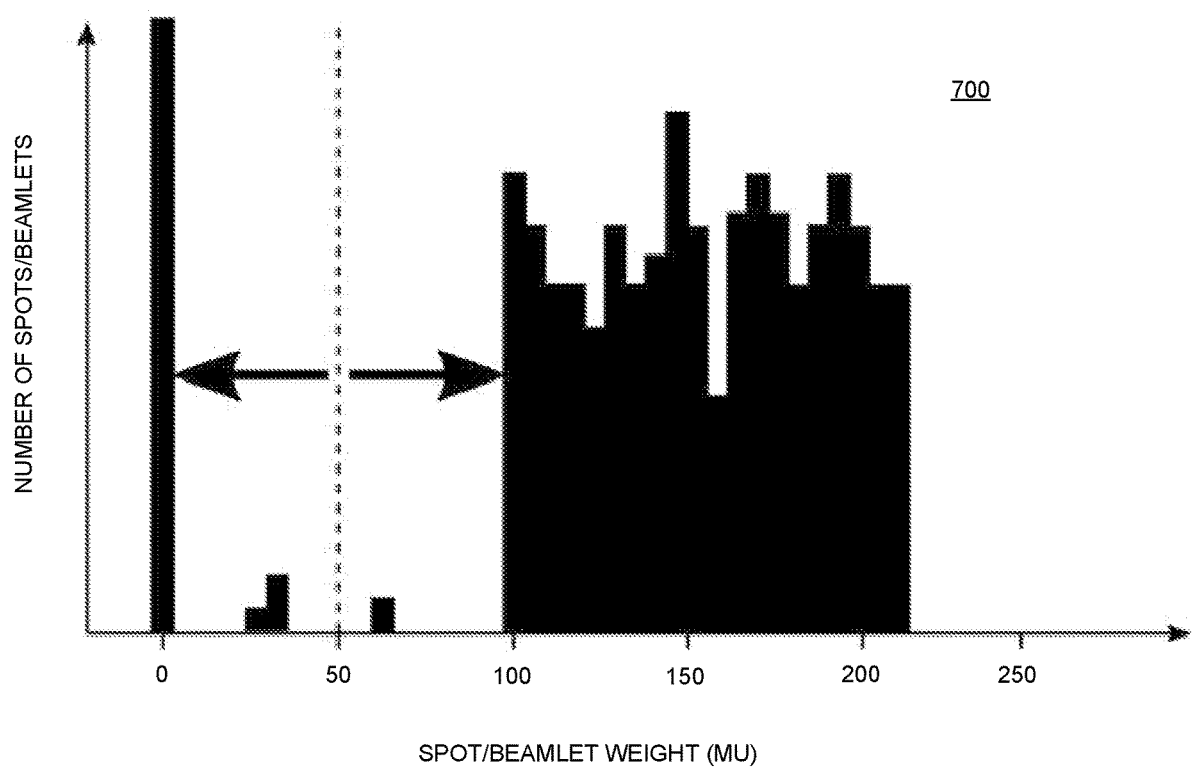
FIG. 7 is a histogram showing another example of the distribution of weights (MUs) that is a result of the use of a minimum MU objective function in radiation treatment planning in embodiments according to the present disclosure.

FIG. 7 is a histogram 700 showing another example of the distribution of spot or beam let weights (MUs) that is a result of the use of the minimum MU objective function 500 of FIG. 5 in the optimization process. In this example, the output of the optimization process includes spots or beam lets with MUs between a value of zero and 100. This result can occur because the minimum MU objective function introduces a "soft" constraint to the optimization process that penalizes spots or beam lets that have a weight (MU) between zero and the minimum threshold value, versus a "hard" constraint that automatically removes such spots or beamlets.

In embodiments, the weights of spots or beamlets that have a spot weight or beam let weight (MU) between zero and the minimum threshold value after optimization are adjusted. In an embodiment, the weights of such spots or beamlets are set to either zero or to the minimum threshold value. In the example of FIG. 7, spot weights or beam let weights that are less than one-half of the minimum threshold value are set to zero, and spot weights or beamlet weights that are greater than or equal to one-half of the minimum threshold value are set to the minimum threshold value. However, the disclosed invention is not limited to the use of one-half as the cutoff as in the example just described.

Other approaches can be used when there are spot weights or beam let weights between zero and the minimum threshold value after optimization. For example, the shape of the minimum MU objective function can be changed.

Adjusting the weights of spots or beam lets that have a spot weight or beam let weight between zero and the minimum threshold value after optimization is optional. As examples, a decision on whether to adjust spot weights or beam let weights can be made based on the impact of those spots or beam lets on delivery (treatment) time, or based on the impact on a dose-volume histogram of adjusting the weights of those spots or beam lets generated for the treatment plan being optimized, or based on the number of such spots or beam lets.

The descriptions above can be extended to include embodiments in which a maximum threshold value is also specified and a maximum MU objective function is also formulated to penalize spots or beamlets that have weights greater than or equal to the maximum threshold value. For example, a maximum MU objective function can be configured (formulated) to determine a value of a term that can be added to the value of the dose metric f_D to account for spots or beamlets that have a weight that is greater than or equal to the maximum threshold value. The formula outputs a value of zero for a spot or a beamlet with a weight between the minimum and maximum threshold values, and a value greater than zero for a spot or a beamlet with a weight greater than or equal to the maximum threshold value. The maximum MU objective function can be combined with the minimum MU objective function into a single objective function.

Figure 8:
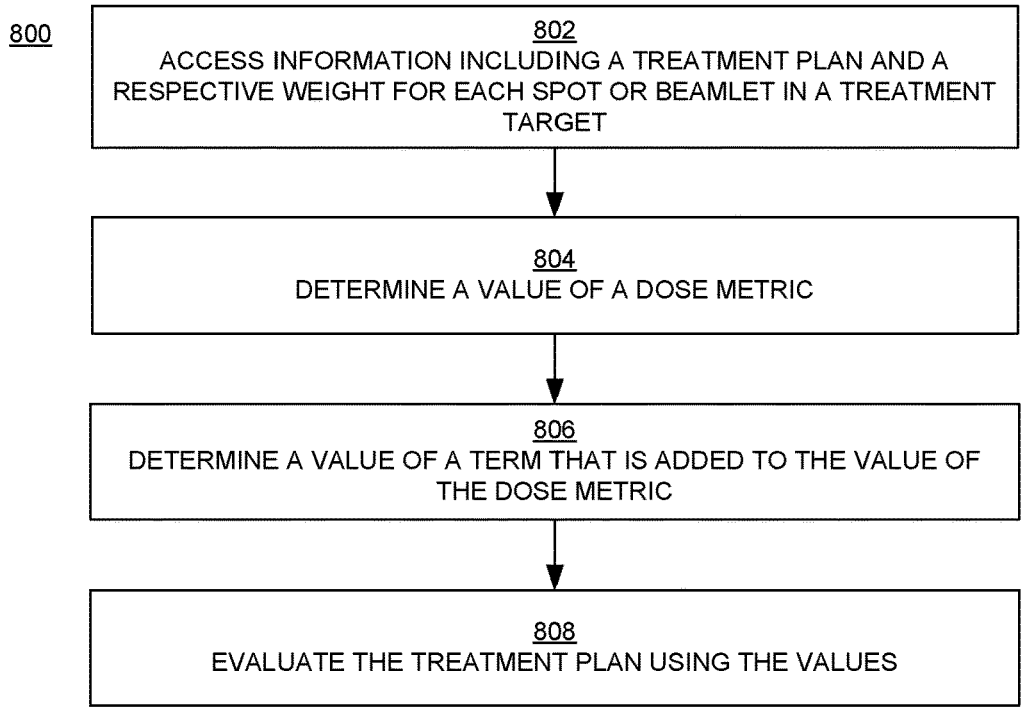
FIGS. 8 and 9 are flowcharts of examples of computer-implemented methods for radiation treatment planning in embodiments according to the present disclosure.
Figure 9:
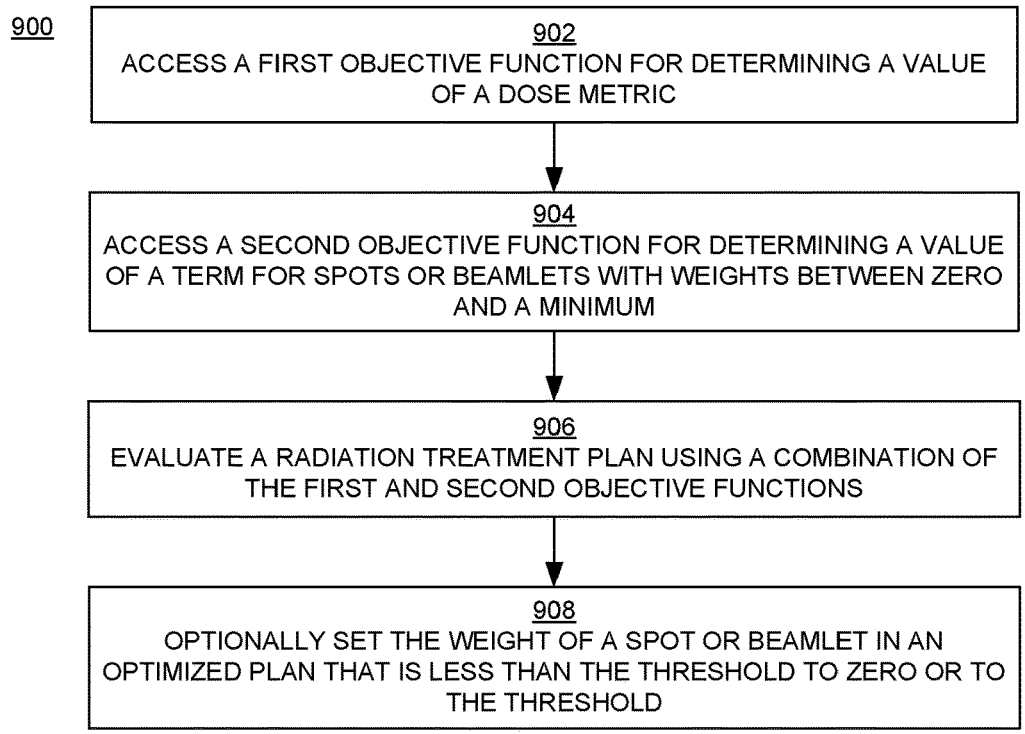

FIGS. 8 and 9 are flowcharts 800 and 900, respectively, of examples of a computer-implemented methods for radiation treatment planning in embodiments according to the present disclosure. The flowcharts 800 and 900 can be implemented as computer-executable instructions (e.g., the TPS 150 of FIG. 1) residing on some form of computer-readable storage medium (e.g., in memory of the computer system 100 of FIG. 1).

While the operations in the flowcharts of FIGS. 8 and 9 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computer system 100 (FIG. 1) for radiation treatment planning as disclosed herein is important.

In block 802 of FIG. 8, a radiation treatment plan is accessed from computer system memory. The treatment plan includes a respective weight assigned to each spot or beamlet inside a treatment target. As discussed above, a spot weight or a beam let weight can each be referred to as a locational weight, with reference to a location that is or may be inside the treatment target.

In block 804, a value of a dose metric for the radiation treatment plan is determined (e.g., with the dose-based objective function f_D).

In block 806, a value of a term that is a function of spot weights or beamlet weights is determined (e.g., with the minimum MU objective function f_MU), and that value is added to the value of the dose metric. The value of the term is greater than zero when the treatment plan includes spots or beam lets that have a weight that is greater than zero and less than a minimum threshold value.

In block 808, the radiation treatment plan is evaluated using (but not limited to) the sum of the values of the dose metric and the term.

In block 902 of FIG. 9, a first objective function (e.g., the dose-based objective function f_D), configured for determining the value of the dose metric, is accessed from computer system memory.

In block 904, a second objective function (e.g., the minimum MU objective function f_MU), configured for determining the value of a term that accounts for spots or beam lets that have weights between zero and a minimum threshold value, is also accessed from computer system memory. In an embodiment, the value of the second objective function is: equal to zero when the value of the MU (e.g., spot weight or beamlet weight) for a spot or a beam let is equal to zero; equal to zero when the value of the MU for a spot or a beamlet is equal to or greater than the minimum threshold value; and greater than zero when the value of the MU for a spot or a beamlet is between zero and the minimum threshold value. The value of the term determined with the second objective function is the summation of these values across all the spots or beam lets.

In block 906, a radiation treatment plan is evaluated using an objective function that includes (but is not limited to) a combination of the first objective function and the second objective function.

In embodiments, the evaluation of blocks 808 and 906 includes optimizing (e.g., determining the minimum value of) a total objective function that includes a summation of objective functions including the combination of the first objective function and the second objective function, to produce a final (optimized) radiation treatment plan that includes final weights for the spots or beamlets.

In block 908, in an embodiment, if the optimized radiation treatment plan includes a spot or a beam let that has a weight that is less than the minimum threshold value, then the weight of that spot or beamlet is optionally set to either zero or the minimum threshold value.

While embodiments disclosed herein generate optimized treatment plans for proton, ion, and photon therapy, embodiments of the present invention are also well-suited to other forms of radiotherapy treatment (such as electron beams or atom nuclei beams (e.g., carbon, helium, and lithium)).

The methodologies disclosed herein may also be useful for stereotactic radiosurgery as well as stereotactic body radiotherapy with single or multiple metastases.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
   a processor; and
   memory coupled to the processor and comprising instructions that, when executed, cause the processor to perform a method used for planning radiation treatment of a treatment target, the method comprising:
      accessing, from the memory, a radiation treatment plan for the treatment target;
      determining a value of a dose metric using information in the radiation treatment plan;
      adding, to the value of the dose metric, a value of a term that is determined using weights corresponding to respective locations in the treatment target, wherein the value of the term is greater than zero when a weight corresponding to a location in the treatment target is greater than zero and less than a minimum threshold value; and
      evaluating the radiation treatment plan using a sum of the values of the dose metric and the term.

2. The computer system of claim 1, wherein said determining, adding, and evaluating comprise:
   accessing, from the memory, a first objective function configured for determining the value of the dose metric;
   accessing, from the memory, a second objective function configured for determining the value of the term; and
   evaluating the radiation treatment plan using an objective function comprising a combination of the first objective function and the second objective function.

3. The computer system of claim 2, wherein said evaluating the radiation treatment plan comprises minimizing a total objective function comprising a summation of a plurality of objective functions including the combination of the first objective function and the second objective function, to produce a final radiation treatment plan comprising final weights corresponding to the locations in the treatment target.

4. The computer system of claim 1, wherein the value of the term is equal to a sum of values determined using the weights, wherein the value of the term is equal to zero when the weights are each equal to zero, wherein the value of the term is equal to zero when the weights are each equal to or greater than the minimum threshold value, and wherein otherwise the value of the term is greater than zero.

5. The computer system of claim 1, wherein the value of the term is also greater than zero when the weight is greater than a maximum threshold value.

6. The computer system of claim 1, wherein the weights are selected from the group consisting of: spot weights for spots at the locations in the treatment target, and beam let weights for beamlets of a beam that are directed into the locations in the treatment target during radiation treatment; wherein a weight of a spot is based on a value selected from the group consisting of: a number of monitor units for the spot, and a number of protons for the spot; and wherein a weight of a beamlet is based on a value selected from the group consisting of: a fraction of an energy of the beam, a percentage of an energy of the beam, a fraction of an intensity of the beam, and a percentage of an intensity of the beam.

7. The computer system of claim 1, wherein the method further comprises:
   after said evaluating the radiation treatment plan is performed, identifying a weight corresponding to a location in the treatment target and that is less than the minimum threshold value; and setting the weight that is less than the minimum threshold value to a value selected from the group consisting of: zero; and the minimum threshold value.

8. A computer system, comprising:
a processor; and
memory coupled to the processor and comprising instructions that, when executed, cause the processor to perform a method used for planning radiation treatment of a treatment target, the method comprising:
    accessing, from the memory, information comprising a radiation treatment plan for the treatment target; and
    optimizing the radiation treatment plan using an objective function comprising a combination of a first objective function and a second objective function, wherein the first objective function is configured for determining a value of a dose metric for the treatment target based on information in the radiation treatment plan, wherein the second objective function is configured for determining a value of a term that is a function of weights corresponding to locations in the treatment target, and wherein the value of the term is greater than zero when a weight corresponding to a location in the treatment target is greater than zero and less than a minimum threshold value.

9. The computer system of claim 8, wherein the value of the term is equal to a sum of values determined using the weights, wherein the value of the term is equal to zero when the weights are each equal to zero, wherein the value of the term is equal to zero when the weights are each equal to or greater than the minimum threshold value, and wherein otherwise the value of the term is greater than zero.

10. The computer system of claim 8, wherein the weights are selected from the group consisting of: spot weights for spots at the locations in the treatment target, and beam let weights for beamlets of a beam that are directed into the locations in the treatment target during radiation treatment; wherein a weight of a spot is based on a value selected from the group consisting of: a number of monitor units for the spot, and a number of protons for the spot; and wherein a weight of a beamlet is based on a value selected from the group consisting of: a fraction of an energy of the beam, a percentage of an energy of the beam, a fraction of an intensity of the beam, and a percentage of an intensity of the beam.

11. The computer system of claim 8, wherein said optimizing comprises minimizing a total objective function comprising a summation of a plurality of objective functions including the combination of the first objective function and the second objective function.

12. The computer system of claim 8, wherein the method further comprises:
    after said optimizing, identifying a weight corresponding to a location in the treatment target and that is less than the minimum threshold value; and
    setting the weight that is less than the minimum threshold value to a value selected from the group consisting of: zero; and the minimum threshold value.

13. The computer system of claim 8, wherein the value of the term is also greater than zero when the weight is greater than a maximum threshold value.

14. The computer system of claim 8, wherein said optimizing produces a final radiation treatment plan comprising final weights corresponding to the locations in the treatment target.

15. A computer-implemented method used for used for planning radiation treatment of a treatment target, the method comprising:
    accessing, from memory of a computer system, information comprising a candidate radiation treatment plan for the treatment target;
    accessing a first objective function configured for determining a dose metric;
    accessing a second objective function configured for determining a value of a term using weights corresponding to locations in the treatment target, wherein the value of the term is greater than zero when a weight corresponding to a location in the treatment target is greater than zero and less than a minimum threshold value; and
    optimizing the candidate radiation treatment plan using an objective function comprising a combination of the first objective function and the second objective function, wherein said optimizing comprises optimizing a total objective function comprising a summation of a plurality of objective functions including the combination of the first objective function and the second objective function.

16. The computer-implemented method of claim 15, wherein the value of the term is equal to a sum of values determined using the weights, wherein the value of the term is equal to zero when the weights are each equal to zero, wherein the value of the term is equal to zero when the weights are each equal to or greater than the minimum threshold value, and wherein otherwise the value of the term is greater than zero.

17. The computer-implemented method of claim 15, wherein said optimizing produces a final radiation treatment plan comprising final weights corresponding to the locations in the treatment target.

18. The computer-implemented method of claim 15, wherein the weights are selected from the group consisting of: spot weights for spots at the locations in the treatment target, and beamlet weights for beam lets of a beam that are directed into the locations in the treatment target during radiation treatment; wherein a weight of a spot is based on a value selected from the group consisting of: a number of monitor units for the spot, and a number of protons for the spot; and wherein a weight of a beam let is based on a value selected from the group consisting of: a fraction of an energy of the beam, a percentage of an energy of the beam, a fraction of an intensity of the beam, and a percentage of an intensity of the beam.

19. The computer-implemented method of claim 15, further comprising:
    after said optimizing is performed, identifying a weight corresponding to a location in the treatment target and that is less than the minimum threshold value; and
    setting the weight that is less than the minimum threshold value to a value selected from the group consisting of: zero; and the minimum threshold value.

20. The computer-implemented method of claim 15, further comprising increasing, with the second objective function, the weight of a location in the treatment target that has a weight that is greater than a maximum threshold value.

* * * * *